(12) United States Patent
Guillon et al.

(10) Patent No.: US 9,348,128 B2
(45) Date of Patent: May 24, 2016

(54) MICROSCOPE FOR HIGH SPATIAL RESOLUTION IMAGING A STRUCTURE OF INTEREST IN A SAMPLE

(71) Applicants: Marc Guillon, Paris (FR); Marcel Lauterbach, Paris (FR); Valentina Emiliant, Paris (FR)

(72) Inventors: Marc Guillon, Paris (FR); Marcel Lauterbach, Paris (FR); Valentina Emiliant, Paris (FR)

(73) Assignees: INSERM (INSTITUT NATIONAL DE LA SANTÉ ET DE LA RECHERCHE MEDICALE), Paris (FR); CENTRE NATIONAL DE LA RECHERCHE SCIENTIFIQUE—CNRS, Paris (FR); UNIVERSITE PARIS DESCARTES, Paris (FR)

( * ) Notice: Subject to any disclaimer, the term of this patent is extended or adjusted under 35 U.S.C. 154(b) by 0 days.

(21) Appl. No.: 14/394,009

(22) PCT Filed: May 3, 2013

(86) PCT No.: PCT/EP2013/059230
§ 371 (c)(1),
(2) Date: Oct. 10, 2014

(87) PCT Pub. No.: WO2013/167479
PCT Pub. Date: Nov. 14, 2013

(65) Prior Publication Data
US 2015/0076333 A1   Mar. 19, 2015

(30) Foreign Application Priority Data

May 7, 2012   (EP) .................................. 12305509

(51) Int. Cl.
*G02B 21/00* (2006.01)
*G01N 21/64* (2006.01)

(52) U.S. Cl.
CPC ........ *G02B 21/0032* (2013.01); *G01N 21/6402* (2013.01); *G01N 21/645* (2013.01); *G02B 21/0056* (2013.01); *G02B 21/0076* (2013.01); *G01N 2021/6463* (2013.01)

(58) Field of Classification Search
CPC .............. G02B 21/06; G02B 21/0032; G02B 21/0056; G02B 21/0072; G01N 21/6402

USPC ........ 250/216, 234, 458.1, 459.1; 359/205.1, 359/368, 385
See application file for complete search history.

(56) References Cited

U.S. PATENT DOCUMENTS

| | | | |
|---|---|---|---|
| 2007/0206278 A1 | 9/2007 | Dyba et al. | |
| 2010/0176307 A1* | 7/2010 | Hell | G01N 21/636 250/459.1 |
| 2011/0081653 A1* | 4/2011 | Hell | G01N 21/6428 435/6.19 |
| 2011/0140000 A1 | 6/2011 | Iketaki | |

FOREIGN PATENT DOCUMENTS

WO    WO 2010/133678 A1    11/2010

OTHER PUBLICATIONS

International Search Report from related PCT Application under PCT/EP2013/059230; report dated Jun. 6, 2013.

* cited by examiner

*Primary Examiner* — Kevin Pyo
(74) *Attorney, Agent, or Firm* — Miller, Matthias & Hull LLP (57) ABSTRACT

A microscope for high spatial resolution imaging a structure of interest in a sample comprising a substance having a first state with first spectral properties and a second state with second spectral properties, the microscope comprising: an objective-lens assembly, a wave front modulating optical device adapted to spatially vary an intensity of a transfer light beam, a probe detector arranged to detect an optical measurement signal from a portion of the substance in the second state and placed in an area of the transfer light beam with an intensity adapted not to transfer the substance between the first and second states said microscope comprising a phase contrast microscopy system which includes an intensity detector arranged to detect an intensity of an illuminating light beam after said illuminating light beam has passed through the sample, the objective-lens assembly and the wave front modulating optical device.

26 Claims, 8 Drawing Sheets

MICROSCOPE FOR HIGH SPATIAL RESOLUTION IMAGING A STRUCTURE OF INTEREST IN A SAMPLE

CROSS-REFERENCE TO RELATED APPLICATION

This application is a 35 USC §371 U.S. national stage filing of International Patent Application No. PCT/EP2013/059230 filed on May 3, 2013, which claims priority under the Paris Convention to European Patent Application No. EP12305509.7 filed on May 7, 2012.

FIELD OF THE DISCLOSURE

The invention relates to a microscope for high spatial resolution imaging a structure of interest in a sample.

BACKGROUND OF THE DISCLOSURE

Although not limited thereto, the invention especially applies to Stimulated Emission Depletion (STED) microscopy (S. W. Hell and J. Wichmann, Optics Letters 19, 780 (1994); T. A. Klar and S. W. Hell, Optics Letters 24, 954 (1999)) which is an ideal method for imaging with high spatial and temporal resolution. A resolution better than 6 nm (E. Rittweger, K. Y. Han, S. E. Irvine, C. Eggeling, and S. W. Hell, Nature Photonics 3, 144 (2009)) can be reached. STED microscopy allows dynamic imaging (V. Westphal, M. A. Lauterbach, A. Di Nicola, and S. W. Hell, New Journal of Physics 9, 435 (2007)) with up to 200 frames per second (M. A. Lauterbach, C. Ullal, V. Westphal, and S. W. Hell, Langmuir 26, 14400 (2010)) and is compatible with imaging dynamics in living cells (V. Westphal, S. O. Rizzoli, M. A. Lauterbach, D. Kamin, R. Jahn, and S. W. Hell, Science 320, 246 (2008); B. Hein, K. I. Willig, and S. W. Hell, Proceedings of the National Academy of Sciences of the United States of America 105, 14271 (2008)) and even in tissue (U. V. Nägerl, K. I. Willig, B. Hein, S. W. Hell, and T. Bonhoeffer, Proceedings of the National Academy of Sciences of the United States of America 105, 18982 (2008); N. T. Urban, K. I. Willig, S. W. Hell, and U. V. Nägerl, Biophysical Journal 101, 1277 (2011)).

A common implementation of STED microscope is as a laser scanning microscope. The sample to image is provided with a substance, such as a fluorescent marker or fluorophores, having a first state with first spectral properties and a second state with second spectral properties. In particular, the fluorophores emit fluorescence when relaxing from the second state to the first state. In STED microscopy, an excitation focus is provided by a focused laser probing light beam illuminating the sample through an objective-lens assembly. The fluorescence ability of the fluorophores in an outer part of the excitation focus is transiently turned off. The switching of the molecules into a non-fluorescent state is achieved via stimulated emission with a laser transfer light beam ("STED beam"). The STED beam is commonly passed through a spiral phase mask of charge one, sometimes imaged with a 4f configuration onto a back focal plane of an objective-lens assembly, resulting in a toroidal focus having a first intensity area with a first intensity adapted to deplete the fluorophores in the second state to the first state, and a second intensity area with a second intensity adapted not to transfer the fluorophores between the first and second states (V. Westphal, M. A. Lauterbach, A. Di Nicola, and S. W. Hell, New Journal of Physics 9, 435 (2007)). Besides, in STED microscopy, fluorescence can be elicited in the stained sample by the probing light beam overlaid onto the STED focus of toroidal ("donut") shape, at least partly onto the second intensity area. Thus, the ability of the fluorophores to emit is turned off via stimulated emission in the first intensity area corresponding to the periphery of the excitation focus. Only in the second area, at the very center, where the STED focus has close-to-zero intensity, the fluorophores are able to spend significant time in the fluorescent state. The second intensity area wherein the fluorophores are not switched off, and accordingly the minimally resolvable distance, shrink to zero with increasing intensity of the STED beam (S. W. Hell, Science 316, 1153 (2007)). The fluorescence of the fluorophores in the second area of the transfer light beam forms an optical measurement signal detected point by point by a probe detector.

It is, however, often desirable to locate and image structures of interest in a biological specimen as sample, such as cells, which do not strongly absorb light and do not fluoresce. Such structure of interest can hardly be located and imaged using STED microscopy even with the implementation of a second high-resolution color channel.

The invention aims to solve the above mentioned problem.

To that end, the invention proposes a microscope for high spatial resolution imaging a structure of interest in a sample comprising a substance, said substance having a first state with first spectral properties and a second state with second spectral properties, the microscope comprising:
an objective-lens assembly having first and second sides opposite to each other, and presenting first and second focal planes respectively on said first and second sides, the sample being intended to be placed on the first side,
a transfer light source arranged on the second side of the objective-lens assembly to emit a transfer light beam towards the sample through the objective-lens assembly, said transfer light beam having an intensity and a phase profile,
a light beam modulating device placed between the transfer light source and the objective-lens assembly, said light beam modulating device being adapted to spatially vary the transfer light beam so that said transfer light beam having passed trough said light beam modulating device and the objective-lens assembly presents at least a first intensity area with a first intensity adapted to transfer the substance in the second state to the first state, and at least a second intensity area with a second intensity adapted not to transfer the substance between the first and second states,
a probe detector adapted to detect an optical measurement signal from a portion of the substance in the second state,
said microscope comprising a phase contrast microscopy system which includes:
the light beam modulating device further adapted to generate a phase contrast,
an illuminating light source arranged to emit an illuminating light beam towards the sample, said illuminating light beam having an intensity and a phase profile,
an intensity detector arranged to detect the intensity of the illuminating light beam after said illuminating light beam has passed at least once through the sample, the objective lens assembly and the light beam modulating device.

SUMMARY OF THE DISCLOSURE

Hence, the invention provides a high-resolution microscope with improved observation capabilities enabling, through a second contrast channel, to locate and image structures of interest, and especially biological structures of interest, which do not strongly absorb light and do not fluoresce.

Besides, in accordance with the invention, the phase contrast microscopy system uses the same light beam modulating device as used for the high spatial resolution microscopy system, so that only few optical elements are added, thereof none in the transfer light beam path.

In addition, using phase contrast for the second contrast channel eliminates necessity for staining the specimen with a second marker.

The light beam modulating device may be adapted to vary the transfer light beam so that the first intensity area surrounds the second intensity area.

The light beam modulating device may be a phase mask adapted to modulate the phase profiles of the transfer light beam and of the illuminating light beam.

In particular, the light beam modulating device may be a spiral phase mask adapted to apply an angular-dependent phase shift to the phase profiles of the transfer light beam and of the illuminating light beam. With these provisions, spiral phase contrast (SPC) (J. Davis, D. McNamara, D. Cottrell, and J. Campos, Optics Letters 25, 99 (2000); S. Fürhapter, A. Jesacher, S. Bernet, and M. Ritsch-Marte, Optics Express 13, 689 (2005)) using the same type of phase mask as is commonly used for shaping a STED beam can be implemented. When used for high spatial resolution imaging, a toroïdal ("donut") shape can be imparted to the transfer light beam passing through the spiral phase mask, resulting in a tubular first intensity area surrounding the second intensity area. When used for phase contrast microscopy, the spiral phase mask provides locations of destructive interference enabling an enhanced signal to noise ratio.

In a particular embodiment, the microscope may be adapted for Stimulated Emission Depletion (STED) microscopy. In such embodiment, the substance comprises a fluorescent marker emitting fluorescence when relaxing from the second state to the first state, the microscope further comprising a probing light source adapted to emit a probing light beam overlaid with the transfer light beam, said probing light beam having an intensity adapted to transfer the marker in the first state to the second state, the transfer light beam in the first intensity area being adapted to deplete the second state of the marker.

The transfer light beam and the probing light beam can be emitted by a same sole light source. The transfer light source and the probing light source may form a single light source which produces both transfer and probing light beams.

As a variant, the transfer light source and the probing light source can be distinct.

Besides, the transfer light beam and the probing light beam can both pass through the light beam modulating device.

The microscope may further comprise a transfer light scanning arrangement adapted to move the transfer light beam and the sample relative to each other so that the sample can be scanned by the transfer light beam.

The microscope may further comprise an illuminating light scanning arrangement adapted to move the illuminating light beam and the sample relative to each other so that the sample can be scanned by the illuminating light beam.

In an embodiment, the transfer light scanning arrangement may be also used as illuminating light scanning arrangement.

The intensity detector may be a pixelated detector, such as a CCD or CMOS camera.

In an alternative, the intensity detector may be a single pixel detector, such as an avalanche photo-diode or a photomultiplier. This provision, in combination with the use of an illuminating light scanning arrangement, enables to perform phase contrast microscopy in a scanning mode. In such scanning mode, phase contrast imaging and high-resolution imaging may use the same scanning arrangement so that image registration depends only on the registration of point sources and detectors, but no image distortions can occur and images can therefore be expected to be well aligned.

The illuminating light source may comprise a coherent light source, such as a laser device. This provision, in combination with the use of point detector as intensity detector, enables to provide optical sectioning, that is signal removal from planes out of focus.

In an alternative, the illuminating light source may comprise an incoherent light source, such as a light-emitting diode, a mercury vapour lamp or a halogen lamp.

The illuminating light source may be arranged on the first side of the objective-lens assembly at a distance defining a space for placing the sample.

The intensity detector may then be arranged on the second side of the objective-lens assembly.

In an alternative, the illuminating light source may be arranged on the second side of the objective-lens assembly.

A reflective element may be arranged on the first side of the objective-lens assembly at a distance defining a space for placing the sample.

In a variant, the intensity detector may be arranged on the first side of the objective-lens assembly.

In particular, the transfer light beam may be the illuminating light beam.

BRIEF DESCRIPTION OF THE DRAWINGS

Other objects and advantages of the invention will emerge from the following disclosure of particular embodiments of the invention given as non limitative example, the disclosure being made in reference to the enclosed drawings in which.

DETAILED DESCRIPTION OF THE DISCLOSURE

On the Figures, the same reference numbers refer to the same or similar elements.

Figure 1:
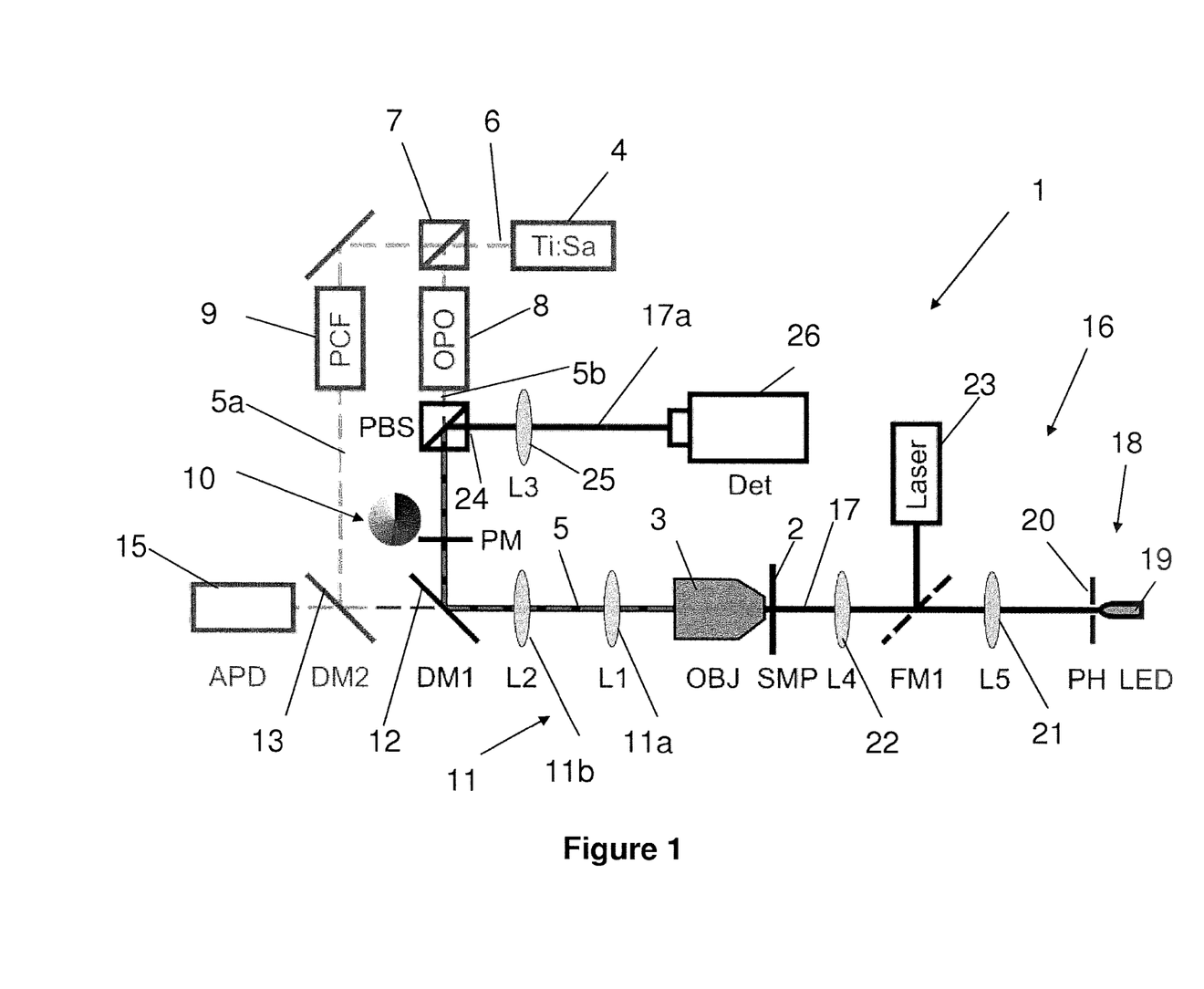
FIG. 1 is a sketch of the main elements of a microscope for high spatial resolution imaging according to a first embodiment of the invention, the microscope implementing an objective-lens assembly, a light source emitting a transfer light beam and a probing light beam, a phase mask and a probe detector for high spatial resolution imaging, and an illuminating light source and an intensity detector for phase contrast imaging, FIG. 2 are phase contrast images obtained by the microscope of FIG. 1 of a sample consisting of small immersion oil droplets on a coverslip, with different positions of the phase mask with respect to an illuminating light beam emitted by the illuminating light source having passed through the sample (A, B, C), and four possible illumination/scanning combinations: incoherent illuminating light beam/wide-field detection (D), incoherent illuminating light beam/scanning detection (E), coherent illuminating light beam/wide-field detection (F), coherent illuminating light beam/scanning detection (G)

FIG. 1 illustrates a microscope 1 for high spatial resolution imaging especially adapted for locating and imaging biological structures of interest, such as biological cells, in a sample 2 (SMP).

In FIG. 1, a Stimulated Emission Depletion (STED) microscope 1 is represented for imaging a structure of interest marked with a fluorescent marker as a substance having a first state with first spectral properties and a second state with second spectral properties. Actually, the fluorescent marker can be repeatedly transferred from a ground state as first state to an excited state as second state, and emits fluorescence when relaxing from the excited state to the ground state.

The microscope 1 comprises an objective-lens assembly 3 (OBJ) having a first or front side and a second or back side, the front and back sides being opposite to each other. On the front side, the objective-lens assembly 3 presents a first or front focal plane in which the sample 2 to be imaged is placed. A second or back focal plane is arranged on the back side of the objective-lens assembly 3.

A light source 4 is arranged on the second side of the objective-lens assembly 3 to emit a light beam 6 towards the sample 2 through the objective-lens assembly 3.

In the illustrated embodiment, the light source 4 comprises a sole laser device adapted to emit the laser beam 6, such as a Ti:Sapphire laser Ti:Sa, and a separator 7 for separating the laser beam 6 into a probing light beam 5a and a transfer light beam 5b. The probing light beam 5a is adapted, especially in terms of intensity and wavelength, for causing an excitation of the fluorescent marker and transferring the fluorescent marker from the ground state to the excited state. Conversely, the transfer light beam 5b is adapted, especially in terms of intensity and wavelength, for causing a de-excitation of the fluorescent marker and depletion of the excited state of the fluorescent marker to the ground state.

Figure 5:
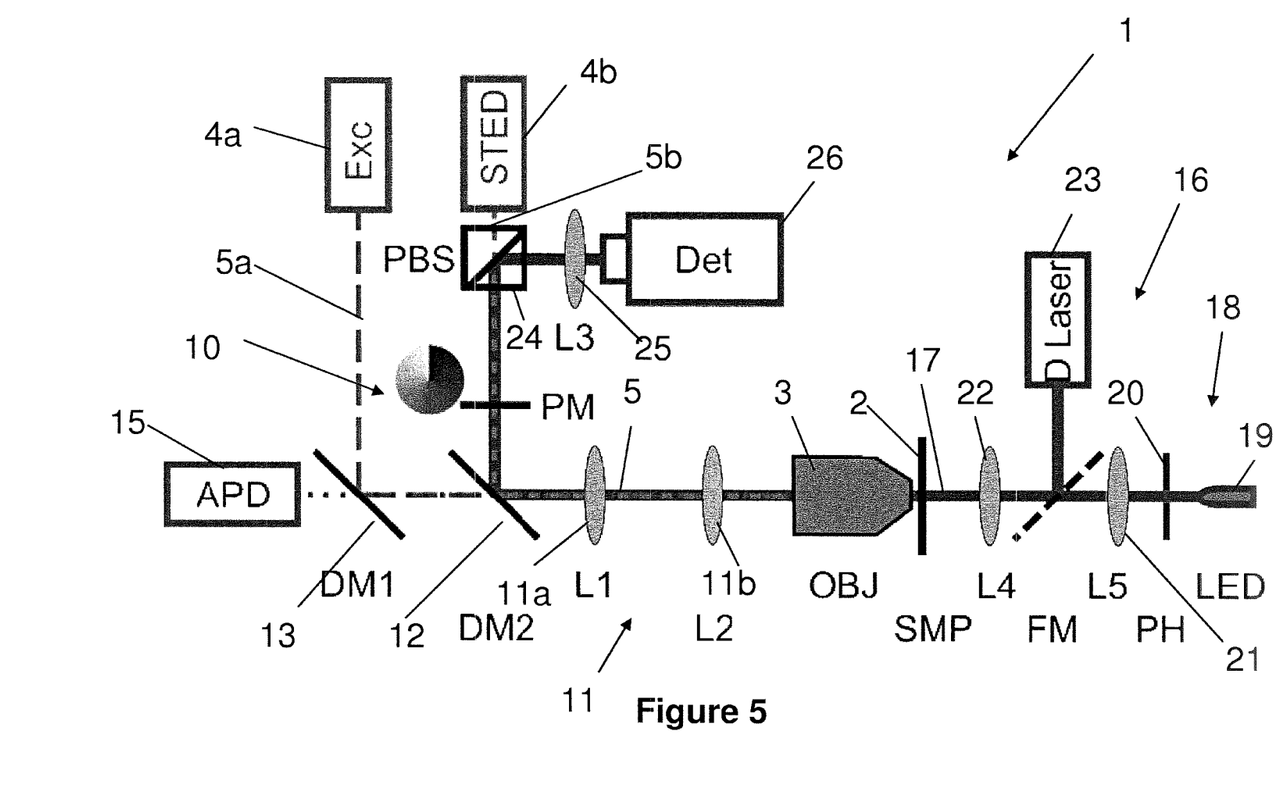
FIG. 5 is a sketch of the main elements of a microscope for high spatial resolution imaging according to a variant of the embodiment of FIG. 1, wherein the transfer light beam and the probing light beam are emitted by two distinct light sources.

In a variant shown on FIG. 5, the probing light beam 5a and the transfer light beam 5b can be emitted separately, respectively by two distinct transfer light (4b) and probing light (4a) sources.

In particular, the laser device pumps an frequency doubled OPO 8 to generate the transfer light beam 5b, or a STED beam in the present embodiment, and a photonic-crystal fiber 9 (PCF) to generate the probing light beam 5a, or a supercontinuum for excitation in the present embodiment. A dielectric filter can be used to select the excitation wavelength. Generation of STED 5b and excitation 5a beams from the same source eliminates potential time jitter (E. Auksorius, B. R. Boruah, C. Dunsby, P. M. P. Lanigan, G. Kennedy, M. A. A. Neil, and P. M. W. French, Optics Letters 33, 113 (2008)). Temporal overlay of the pulsed is adjusted with an optical delay line (not shown).

The STED beam 5b is directed towards the objective-lens assembly 3 through a light beam modulating device 10 placed on the second side of the objective-lens assembly 3, between the light source 4 and the objective-lens assembly 3.

The light beam modulating device 10 is adapted to spatially vary the STED beam 5b, and especially its intensity and/or its phase, so that, once the STED beam 5b has passed trough the light beam modulating device 10 and the objective-lens assembly 3, it presents at least a first intensity area with the nominal intensity adapted to transfer the fluorescent marker in the excited state to the ground state, and at least a second intensity area with a second intensity adapted not to transfer the fluorescent marker between the first and second states. In particular, the second intensity area can have a zero or close-to-zero intensity.

In a preferred embodiment, although not limited thereto, the light beam modulating device 10 is a spiral phase mask (PM) adapted to apply an angular-dependent phase shift to a phase profile of the STED beam 5b. For example, such spiral phase mask 10 may consist of a reflective or transmissive plate extending generally perpendicularly to the optical axis and presenting to opposite transverse surfaces at least one of which being helical around the optical axis. Such spiral phase mask 10 is able to generate a toroidal focus of the STED beam 5b so that so that the first intensity area of the intensity suitable for depletion of the excited state of the fluorescent marker continuously surrounds the second intensity area of zero or close-to-zero intensity.

In other embodiments, the light beam modulating device 10 could be any other kind of phase mask adapted to modulate or change the phase profile of the transfer light beam, preferably so that the first intensity area at least partly surrounds the second intensity area. The light beam modulating device 10 could also be any other spatial light modulator.

A telescope 11 comprising first 11a and second 11b lenses (L1 and L2) in 4f configuration images the back focal plane of the objective-lens assembly 3 onto the phase mask 10 in order to have the phase mask 10 in the Fourier plane of the objective-lens assembly 3.

The STED beam 5b passes the spiral phase mask 10 to generate the toroidal focus in the sample 2. The excitation beam 5a is combined with the STED beam 5b so as to be overlaid with at least with a part of the second area of the STED beam 5b through a first dichroic mirror 12 (DM1). The excitation 5a and STED 5b beams thereby form a switch light beam 5 illuminating the sample 2.

The microscope 1 further comprises a transfer light scanning arrangement adapted to move at least the transfer light beam 5b and the sample 2 relative to each other so that the sample 2 can be scanned by the switch light beam 5. In a variant, the transfer light scanning arrangement may move both the transfer 5*b* and probing 5*a* light beams forming switch light beam 5 and the sample 2 relative to each other. The transfer light scanning arrangement can comprise a scanner adapted to change the orientation of the transfer light beam 5*b* (of the switch light beam 5) and/or a movable support on which the sample 2 is mounted. In the illustrated embodiment, the sample is scanned with a piezo stage.

In doing so, at the center of the switch light beam 5, the fluorescence of the fluorescent marker can be elicited by the excitation beam 5*a* overlaid onto the zero or close-to-zero intensity area of the STED beam 5*b*. On the contrary, at the periphery of the switch light beam 5, the ability of the fluorescent marker to emit is turned off via stimulated emission by the tubular first intensity area of the STED beam 5*b*.

The switch light beam 5 is separated from fluorescence with a second dichroic mirror 13 (DM2). A probe detector 15, such as an avalanche photo diode (APD), is arranged on the second side of the objective-lens assembly 3 to detect the fluorescence of the fluorescent marker as an optical measurement signal.

According to the invention, the above disclosed STED microscope 1 implements spiral phase contrast (SPC).

To that end, the microscope 1 further comprises an illuminating light source 16 arranged to emit an illuminating light beam 17 towards the sample 2 from the first side of the objective-lens assembly 3.

On FIG. 1, the illuminating light source 16 is arranged on the first side of the objective-lens assembly 3 at a distance defining a space for placing the sample 2. The illuminating light source 16 comprises an incoherent light source 18, such as a light-emitting diode 19 (LED) (wavelength 630 nm) arranged behind a plate 20 provided with an aperture (pinhole PH) for Köhler illumination. In a variant, the incoherent light source 18 could be mercury vapour lamp, a halogen lamp or other. A lens 21 (L5) serves as collector and a lens 22 (L4) focuses the illuminating light beam 17 onto the sample 2. In the illustrated embodiment, the illuminating light source 16 also comprises a coherent light source 23, such as a laser device. The sample 2 can be illuminated with either of the incoherent 18 and coherent 23 light sources. In alternatives, the illuminating light source 16 could comprise only one of the incoherent 18 and coherent 23 light sources.

The phase mask 10 is placed in the Fourier plane of the objective-lens assembly 3 for an isotropic contrast enhancement for amplitude and phase objects. It was demonstrated that SPC with coherent laser illumination allows visualizing weak phase objects such as cells (A. Jesacher, S. Fürhapter, S. Bernet, and M. Ritsch-Marte, Physical Review Letters 94 (2005)). Recently a LED, with a spectrum filtered to 1 nm was used to image biological specimen (G. Situ, M. Warber, G. Pedrini, and W. Osten, Optics Communications 283, 1273 (2010)) and SPC with a superluminescent diode was demonstrated (S. Schausberger, B. Heise, C. Maurer, S. Bernet, M. Ritsch-Marte, and D. Stifter, Optics letters 35, 4154 (2010)).

A polarizing beam splitter 24 (PBS) arranged on the second side of the objective-lens assembly 3 separates the STED beam 5*b* and the phase contrast beam 17*a* composed of the illuminating light beam 17 having passed through the sample 2, the objective-lens assembly 3 and the phase mask 10.

A Lens 25 (L3) forms the phase contrast image on an intensity detector 26 (Det) arranged on the second side of the objective-lens assembly 3 to detect an intensity of the phase contrast beam 17*a*.

The intensity detector 26 can be a pixelated detector, such as a CCD or CMOS camera, to enable wide-field detection.

In a preferred variant, the intensity detector 26 can be a single pixel detector, such as an avalanche photo-diode or a photomultiplier. Advantageously, the microscope 1 may then further comprise an illuminating light scanning arrangement adapted to move the illuminating light beam 17 and the sample 2 relative to each other so that the sample 2 can be scanned by the illuminating light beam 17. As for the switch light scanning arrangement, illuminating light scanning arrangement can comprise a scanner adapted to change the orientation of the illuminating light beam 17 and/or the movable support on which the sample 2 is mounted. Such provisions enable implementation of SPC in a scanning mode. As it will become apparent from the following of the description, illuminating light scanning arrangement can be formed by the transfer light scanning arrangement.

In the disclosed embodiment, the implemented phase contrast modality is of spiral type thanks to the use of a spiral phase mask 10 in the STED microscope. Any other type of phase contrast modality could, however, be implemented depending on the phase mask 10, and more generally the light beam modulating device, of the high resolution microscope.

Figure 2:
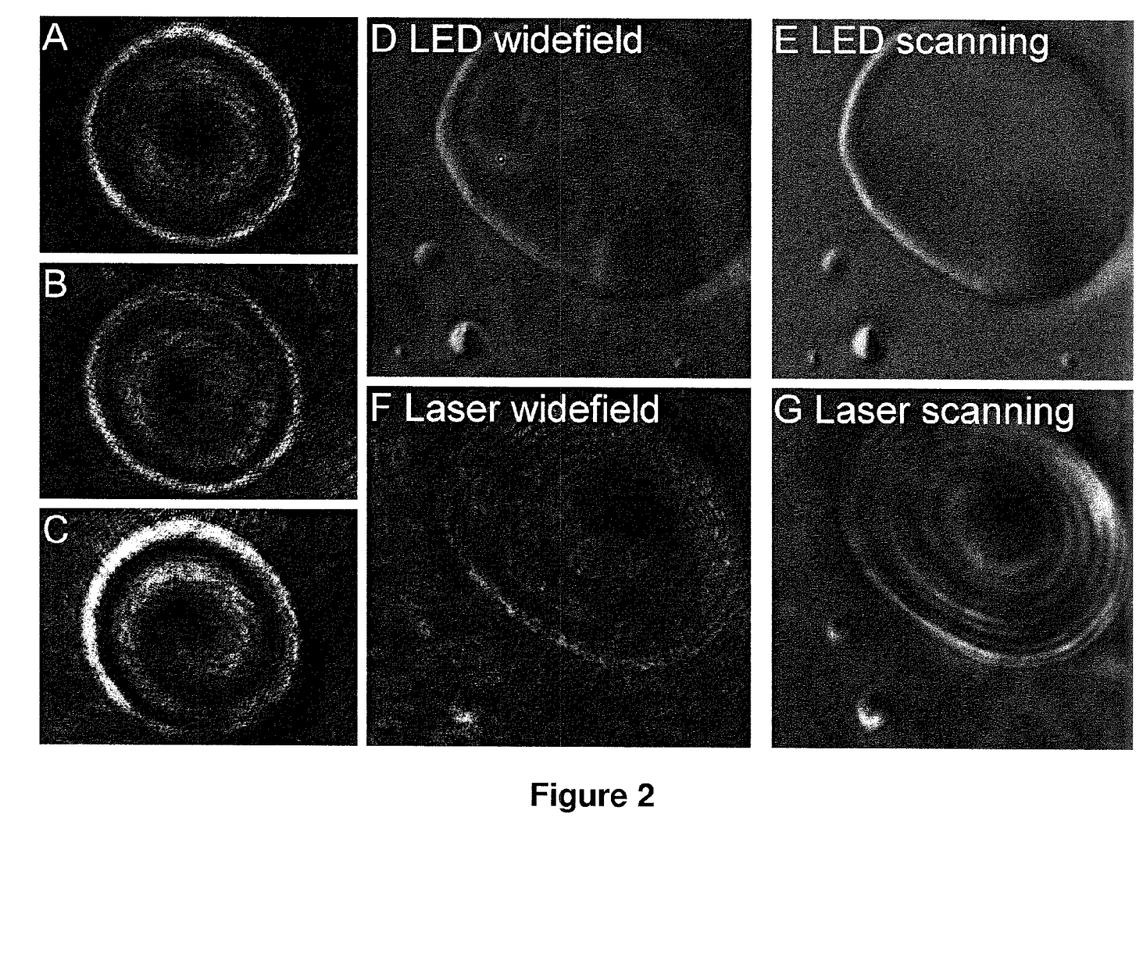

A characterization of SPC itself is shown on FIG. 2 in which small immersion oil droplets on a coverslip, which give a strong phase contrast, were used as test sample. The same region of interest was recorded with the four possible illumination/scanning combinations: incoherent LED illumination, wide-field detection (FIG. 2D); incoherent LED illumination, scanning detection (FIG. 2E); coherent laser illumination, wide-field detection (FIG. 2F); coherent laser illumination, scanning detection (FIG. 2G). Also the position of the phase mask with respect to the illuminating beam of a coherent illumination was studied (FIGS. 2A, 2B and 2C).

On FIGS. 2A, 2B and 2C, it is shown that coherent illumination (laser) leads to spirals, whose starting point depends on the slight de-centering of the phase mask. The starting point of the spirals with coherent illumination depends on this position. If the singularity and, in the present case, the helical shape of the plate, of the phase mask is centered on the illuminating beam, the spiral phase contrast does not lead to spiral but to its degenerate from, concentric rings (FIG. 2A). Slightly offsetting the phase mask leads to spirals, whose starting points depend on the phase mask position (FIGS. 2B and 2C).

On FIGS. 2D, 2E, 2F and 2G, comparing wide-field and scanning modes, for incoherent illumination (LED), essentially no differences are seen (FIGS. 2D and 2E). In contrast, coherent illumination (laser) leads in wide-field configuration to strong background of interference fringes originating from reflections on various surfaces in the optical path (FIG. 2F). In scanning configuration, this background is more homogeneous and constant irrespective of the sample position because shadows that do not originate from the sample are constant over the whole image, so that the image quality is improved in scanning configuration (FIG. 2G). A constant offset in the images is removed for display (contrast stretching), but images are not saturated. Scanned images were recorded with 50 nm pixels.

On FIGS. 3*a* and 3*b*, phase contrast images of neurons obtained by the above disclosed microscope are shown. On FIG. 3*a*, the image is obtained with incoherent illumination and wide-field detection, whereas on FIG. 3*b*, the image is obtained with incoherent illumination and scanning detection. On FIG. 3*c*, an image obtained by a conventional confocal fluorescence microscopy of a region of interest selected from the phase contrast images of FIGS. 3*a* and 3*b* is shown. On FIGS. 3*d* and 3*e*, an image of the same region of interest obtained by high-resolution STED microscopy with the previously disclosed microscope is shown, noise having been suppressed by Wiener filtering on FIG. 3e (on FIG. 3d, the inset shows an intensity profile according to the white bar).

Figure 3:
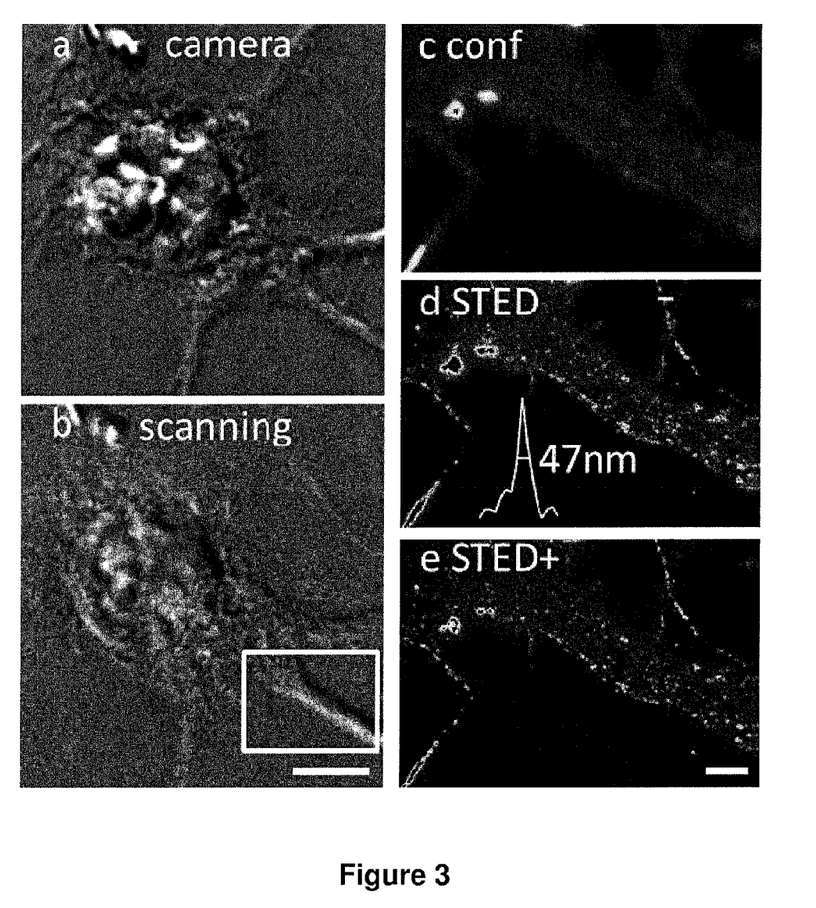
FIG. 3 shows (a) a phase contrast image of neurons obtained by the microscope of FIG. 1 with incoherent illumination and wide-field detection, (b) a phase contrast image of neurons obtained by the microscope of FIG. 1 with incoherent illumination and scanning detection, (c) an image of a region of interest selected from the phase contrast images obtained by a conventional confocal fluorescence microscopy and (d, e) STED images of the region of interest obtained by the microscope of FIG. 1.

As can be seen on FIG. 3, wide-field and scanning SPC may clearly visualizes neurons including flat details such as neuritis and allows for the selection of a region of interest to be imaged in conventional confocal fluorescence microscopy or in high-resolution STED microscopy.

On FIGS. 4a and 4b, scanning SPC images of an astrocyte obtained by the microscope of FIG. 1 are shown. On FIGS. 4c and 4d, images of organelles in embedded astrocytes are obtained by the microscope of FIG. 1 respectively in SPC microscopy and confocal fluorescence microscopy, these two images being superposed on FIG. 4e. On FIGS. 4f, 4g and 4h, images of immunostainded actin filaments are obtained respectively by confocal fluorescence microscopy, STED microscopy implemented by the previously disclosed microscope and confocal SPC implemented by the previously disclosed microscope.

Figure 4:
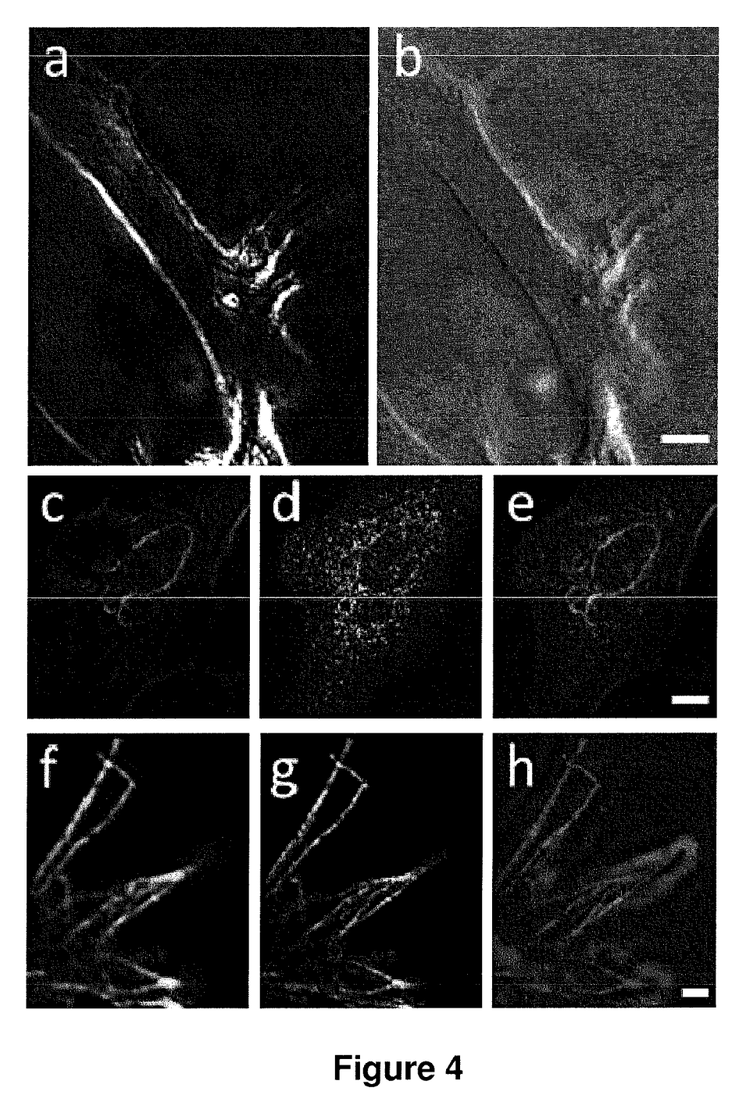
FIG. 4 shows (a, b) scanning SPC images of an astrocyte obtained by the microscope of FIG. 1, (c) an SPC image of organelles in embedded astrocytes obtained by the microscope of FIG. 1, (d) a STED image of organelles in embedded astrocytes obtained by the microscope of FIG. 1, (c) a superposition of the SPC and STED images of organelles in embedded astrocytes obtained by the microscope of FIG. 1, (f) a confocal fluorescence image of immunostainded actin filaments, (g) a STED image of immunostainded actin filaments obtained by the microscope of FIG. 1, (h) confocal SPC image of immunostainded actin filaments obtained by the microscope of FIG. 1.

As can be seen on FIG. 4, confocal SPC imaging visualizes weak phase objects. (a) Symmetrical alignment of scanning SPC highlights contours of an astrocyte in Vectashield on a dark background. (b) Asymmetrical alignment shows the astrocyte with shadow effects on an elevated background like in DIC (differential interference contrast). (c) The contour detection allows for imaging of organelles in embedded astrocytes. (d) Confocal fluorescence imaging of immunostained VAMP3 visualizes vesicles outside organelles. (e) SPC and fluorescence images can be perfectly overlayed. (f) Immunostainded actin filaments in the fine protrusions of the neuronal growth cone of a neurone (confocal fluorescence imaging). (g) STED imaging allows resolving details of the actin organization. (g) Confocal SPC (green) enables visualizing the fine protrusions in phase contrast. The symmetrical contour detection suits for an overlay with the STED image (red). Scale bars: (b) 5 µm; (e) 10 µm; (h) 0.5 µm.

With the microscope of the invention, STED (or confocal fluorescence) images can be recorded simultaneously, since for phase contrast imaging an illumination is used that can be separated easily spectrally from the switch light beam. SPC remains in this case possible although the phase mask is not wavelength matched (G. Situ, G. Pedrini, and W. Osten, J. Opt. Soc. Am. A 26, 1788 (2009)). True simultaneous imaging eliminates possible registration mismatch due to drift. Spiral phase contrast is implemented in STED microscope without compromising the STED-imaging capabilities. It serves as a valuable second contrast channel, in particular for biological specimen.

Spiral phase contrast (SPC) is incorporated into a STED microscope 1 with only few additional optical elements. In particular, the same phase mask 10 shapes the STED beam 5b and generates the phase contrast. Imaging of cells with two contrast channels, label-free phase contrast and high-resolution STED microscopy can then be performed.

Figure 6:
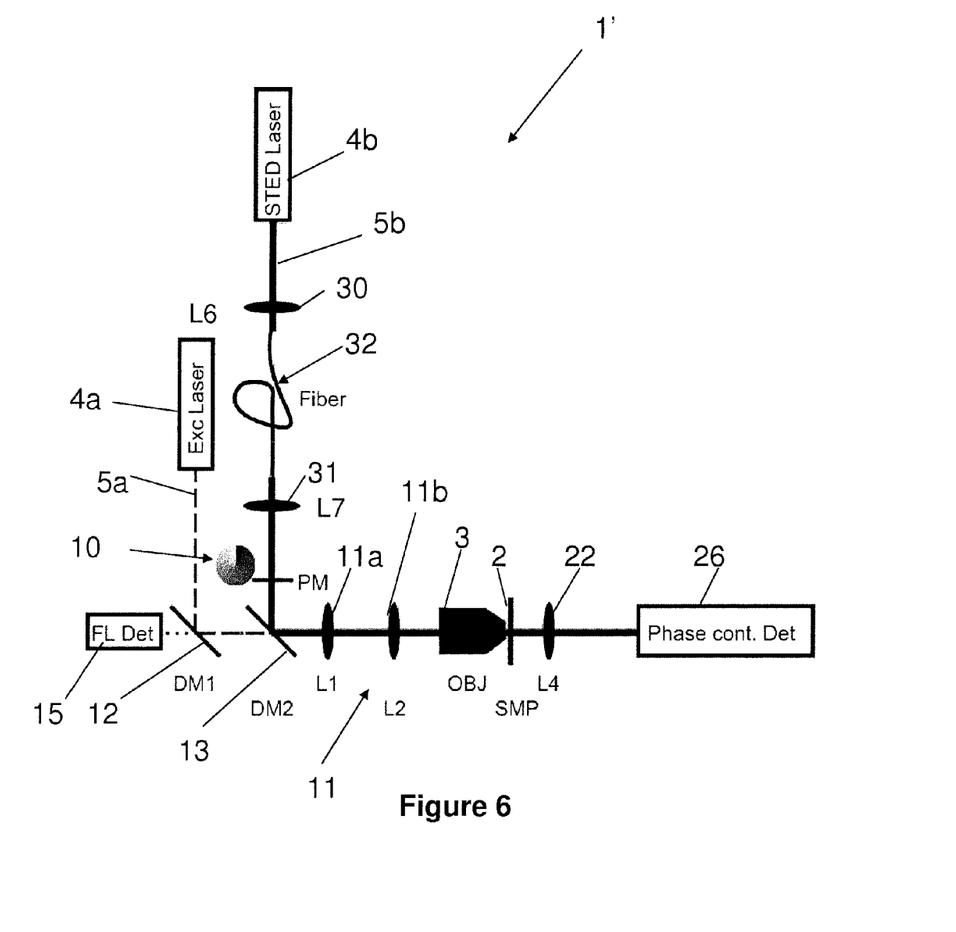
FIG. 6 is a sketch of the main elements of a microscope for high spatial resolution imaging according to a second embodiment of the invention, wherein the transfer light source is also used as illuminating light source for phase contrast in transmission mode.
Figure 7:
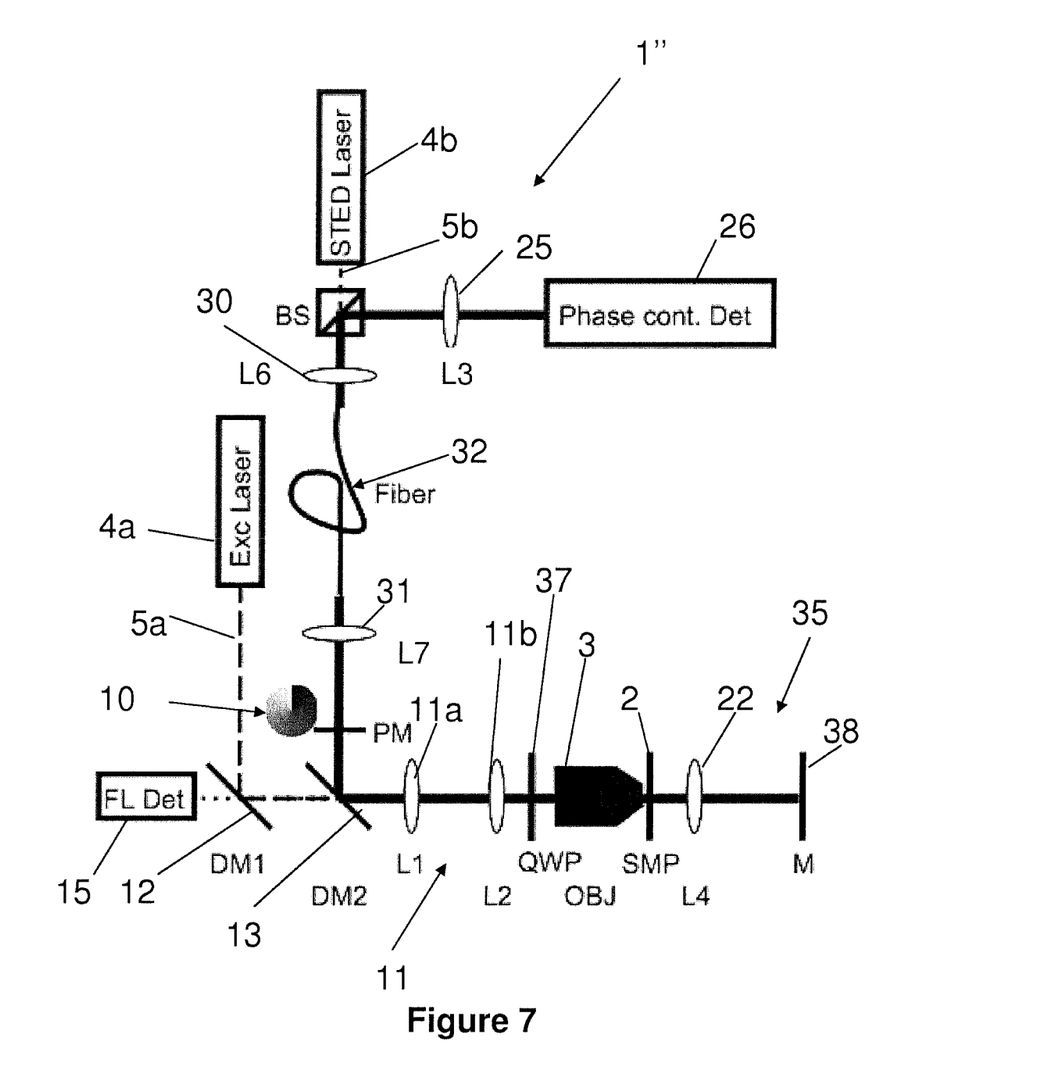
FIG. 7 is a sketch of the main elements of a microscope for high spatial resolution imaging according to a third embodiment of the invention, wherein the transfer light source is also used as illuminating light source for phase contrast together with a retro-reflector.
Figure 8:
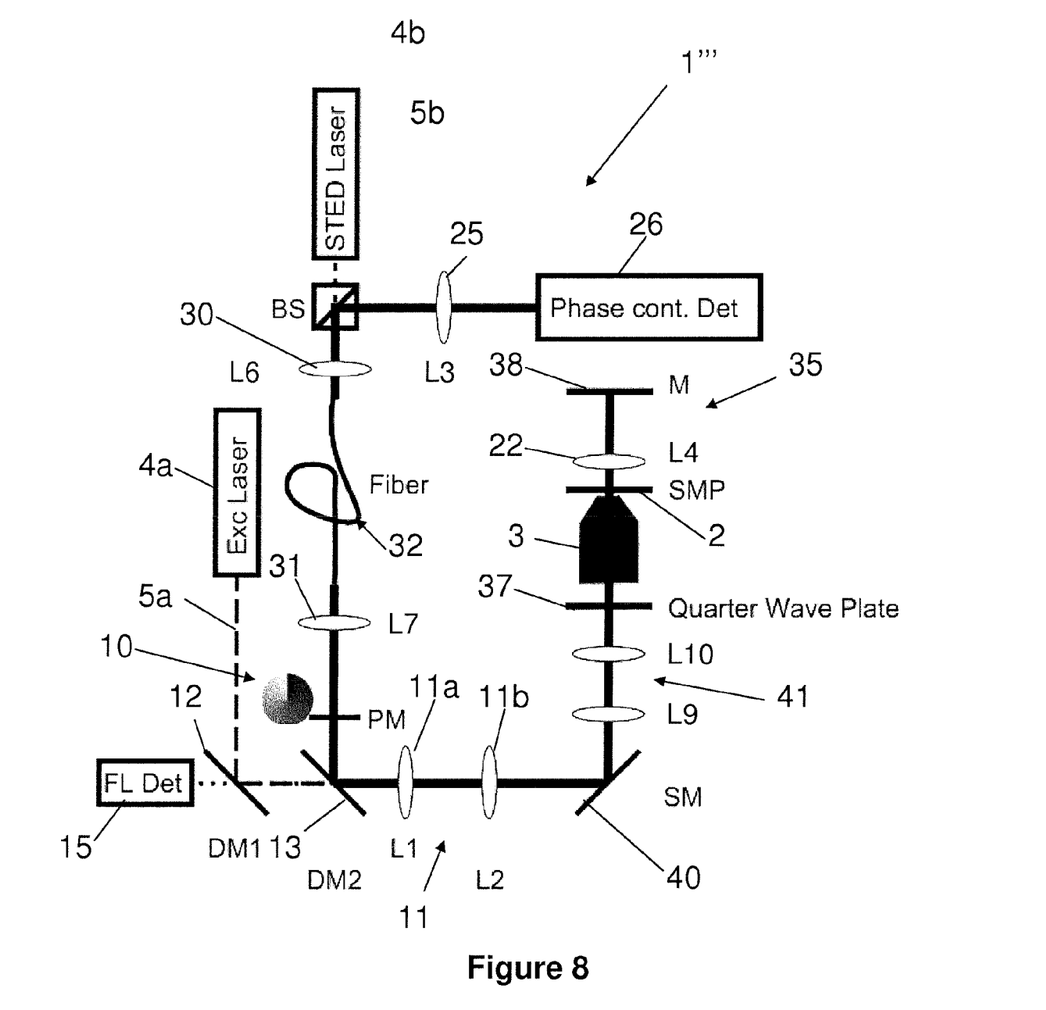
FIG. 8 is a sketch of the main elements of a microscope for high spatial resolution imaging according to a fourth embodiment of the invention, wherein the switch light source is also used as illuminating light source for phase contrast together with a retro-reflector and beam scanning.

In other embodiments shown on FIGS. 6, 7 and 8, the illuminating light source used for phase contrast imaging is arranged on the second side of the objective-lens assembly 3. In particular, the transfer light source 5b is used as the illuminating light source for phase contrast illumination. On FIGS. 6, 7 and 8, although shown as comprising a probing light source 4a (Exc Laser) for emitting the excitation beam 5a and a transfer light source 4b (STED Laser) for emitting the laser beam 5b, only one laser device could be used.

In particular, FIG. 6 shows the use of the STED beam 5b as the illuminating light beam for phase contrast illumination in transmission mode. The microscope 1' according to a second embodiment shown on FIG. 6 mainly differs from that of FIG. 1 in that the intensity detector 26 (Phase cont. Det) is arranged on the first side of the objective-lens assembly 3 to receive the STED beam 5b having passed successively the phase mask 10, the objective-lens assembly 3 and the sample 2. The other parts of the microscope 1' according to the second embodiment are analogous to that already disclosed in relation to the first embodiment. The description will not be repeated and reference is made to the previous description for further details.

In this embodiment, the STED beam 5b is coupled by a lens 30 (L5) into a polarization maintaining fiber 32. This arrangement is used to clean the beam profile of the STED beam 5b and to stretch the pulses temporally. A lens 31 (L7) serves as output coupler. However, it is not mandatory to use a fiber for cleaning and stretching. For example, for spatial cleaning the fiber could be replaced by a pinhole. The STED beam 5b passes the phase mask 10, which is imaged by first 11a and second 11b lenses (L1 and L2) onto the back focal plane of the objective-lens assembly 3.

For high-resolution fluorescence imaging, the fluorescent marker is excited in the sample 2 by excitation beam 5a and fluorescence is detected by the probe detector 15 (FL Det). As explained above, fluorescent marker in same regions can be kept dark by the STED beam 5b.

For phase contrast imaging, the light source 4b that emits the STED beam 5b is also used for the illumination beam for the phase contrast: The light of the STED light source 4b that has passed the sample 2 is imaged onto the intensity detector 26. In contrast to the implementation shown on FIG. 1, the illumination light for the phase contrast passes first the phase mask 10 and then the sample 2.

FIG. 7 shows the use of the STED beam 5b for phase contrast illumination together with a retro-reflector. The microscope 1" according to a third embodiment shown on FIG. 7 mainly differs from that of FIG. 1 in that a reflective element 35 is arranged on the first side of the objective-lens assembly 3 at a distance defining a space for placing the sample 2, so as to reflect the STED beam 5b having passed the objective-lens assembly 3. Again, the other parts of the microscope 1' according to the second embodiment are analogous to that already disclosed in relation to the first embodiment. The description will not be repeated and reference is made to the previous description for further details.

The STED beam 5b passes the polarizing beam splitter 24 (BS). Then as in the second embodiment of FIG. 3, the STED beam 5b is coupled by lens 30 (L6) into the polarization maintaining fiber 32. Lens 31 (L7) serves as output coupler. The STED beam 5b passes the phase mask 10, which is imaged by first 11a and second 11b lenses (L1 and L2) onto the back focal plane of the objective-lens assembly 3. A quarter wave plate 37 (QWP) serves for generating circular polarization in the sample 2.

As for the second embodiment of FIG. 6, for high-resolution fluorescence imaging, the fluorescent marker is excited in the sample 2 by excitation beam 5a and fluorescence is detected by the probe detector 15. As explained above, fluorescent marker in same regions can be kept dark by the STED beam 5b.

For phase contrast imaging, the STED beam 5b is reflected back by the retro-reflector 35 consisting of the lens 22 (L4) and a mirror 38 (M), after having passed the sample 2. Use of a spherical mirror is advantageous but not necessary. The back-traveling beam carries the phase information form the sample 2 that it passed twice. After having passed the phase mask 10 a second time, it is focused by the lens 31 (L7) onto the fiber entry which serves as confocal detection pinhole. When the beam reaches the fiber 32 its polarization is turned by 90° due to the double passage through the quarter wave plate 37. The light exits the polarization maintaining fiber therefore also with turned polarization and is reflected by the polarizing beam splitter 24 towards the intensity detector 26. In variants, other types of retro-reflectors could be used.

This configuration has the advantage that the STED beam and the confocal phase contrast detection are perfectly aligned because the same fiber (or pinhole) emits the STED beam and serves as confocal pinhole.

FIG. 8 shows the use of the STED beam 5b for phase contrast illumination together with a retro-reflector 35 and beam scanning. The microscope 1''' according to a fourth embodiment shown on FIG. 8 mainly differs from the third embodiment of FIG. 7 in that a scan mirror 40 (SM) allows for scanning the illuminating beam over the sample 2. A second telescope 41 consisting of two lenses (L9 and L10) images the scan mirror onto the aperture of the objective-lens assembly 3. Again, the other parts of the microscope 1''' according to the fourth embodiment are analogous to that already disclosed in relation to the first embodiment. The description will not be repeated and reference is made to the previous description for further details.

The above description of the invention has been made with a microscope of Stimulated Emission Depletion (STED) type together with a substance comprising a fluorescent marker. The invention is, however, not limited to STED microscopy and could be implemented, more generally, in any other kind of microscopy, such as Reversible Saturable Optical Fluorescence Transitions (RESOLFT) microscopy, in which the switch light beam includes a transfer light beam which, once passed through the wave front modulating optical device, presents a first area with a first intensity adapted to transfer the substance in a second state with second spectral properties to a first state with first spectral properties, and at least a second area with a second intensity adapted not to transfer the substance between the first and second states. The substance is chosen accordingly among substances having first and second states of which the respective spectral properties comprise a distinguishing features selected from:

- an altered optical absorption of a probe beam,
- an altered polarization property for a probe beam,
- an altered luminescence selected from fluorescence, phosphorescence, electro-luminescence and chemo-luminescence.

The invention claimed is:

1. A microscope for high spatial resolution imaging a structure of interest in a sample comprising a substance, said substance having a first state with first spectral properties and a second state with second spectral properties, the microscope comprising:
   - an objective-lens assembly having first and second sides opposite to each other, and presenting first and second focal planes respectively on said first and second sides, the sample being intended to be placed on the first side,
   - a transfer light source arranged on the second side of the objective-lens assembly to emit a transfer light beam towards the sample through the objective-lens assembly, said transfer light beam having an intensity and a phase profile,
   - a light beam modulating device placed between the transfer light source and the objective-lens assembly, said light beam modulating device being adapted to spatially vary the transfer light beam so that said transfer light beam after having passed trough said light beam modulating device and the objective-lens assembly presents at least a first intensity area with a first intensity adapted to transfer the substance in the second state to the first state, and at least a second intensity area with a second intensity adapted not to transfer the substance between the first and second states,
   - a probe detector adapted to detect an optical measurement signal from a portion of the substance in the second state,
   - wherein said microscope comprises a phase contrast microscopy system which includes:
   - the light beam modulating device further adapted to generate a phase contrast,
   - an illuminating light source arranged to emit an illuminating light beam towards the sample, said illuminating light beam having an intensity and a phase profile,
   - an intensity detector arranged to detect the intensity of the illuminating light beam after said illuminating light beam has passed at least once through the sample, the objective lens assembly and the light beam modulating device.

2. The microscope according to claim 1, wherein the light beam modulating device is adapted to vary the transfer light beam so that the first intensity area surrounds the second intensity area.

3. The microscope according to claim 1, wherein the light beam modulating device being a phase mask adapted to modulate the phase profiles of the transfer light beam and of the illuminating light beam.

4. The microscope according to claim 3, wherein the light beam modulating device is a spiral phase mask adapted to apply an angular-dependent phase shift to the phase profiles of the transfer light beam and of the illuminating light beam.

5. The microscope according to claim 1, wherein the substance comprises a fluorescent marker emitting fluorescence when relaxing from the second state to the first state, the microscope further comprising a probing light source adapted to emit a probing light beam overlaid with the transfer light beam, said probing light beam having an intensity adapted to transfer the marker in the first state to the second state, the transfer light beam in the first intensity area being adapted to deplete the second state of the marker.

6. The microscope according to claim 5, wherein the transfer light source and the probing light source form a single light source which produces both transfer and probing light beams.

7. The microscope according to claim 1, further comprising a transfer light scanning arrangement adapted to move the transfer light beam and the sample relative to each other so that the sample can be scanned by the transfer light beam.

8. The microscope according to claim 1, further comprising an illuminating light scanning arrangement adapted to move the illuminating light beam and the sample relative to each other so that the sample can be scanned by the illuminating light beam.

9. The microscope according to claim 1, wherein the intensity detector is a pixelated detector.

10. The microscope according to claim 1, wherein the intensity detector is a single pixel detector.

11. The microscope according to claim 1, wherein the illuminating light source comprises a coherent light source.

12. The microscope according to claim 1, wherein the illuminating light source comprises an incoherent light source.

13. The microscope according to claim 1, wherein the illuminating light source is arranged on the first side of the objective-lens assembly at a distance defining a space for placing the sample.

14. The microscope according to claim 13, wherein the intensity detector is arranged on the second side of the objective-lens assembly.

15. The microscope according to claim 1, wherein the illuminating light source is arranged on the second side of the objective-lens assembly.

16. The microscope according to claim 15, wherein a reflective element is arranged on the first side of the objective-lens assembly at a distance defining a space for placing the sample.

17. The microscope according to claim 15, wherein the intensity detector is arranged on the first side of the objective-lens assembly.

18. The microscope according to claim 15, wherein the transfer light beam is the illuminating light beam.

19. The microscope according to claim 9, wherein the pixelated detector is a CCD camera.

20. The microscope according to claim 9, wherein the pixelated detector is a CMOS camera.

21. The microscope according to claim 10, wherein the single pixel detector is an avalanche photo-diode.

22. The microscope according to claim 10, wherein the single pixel detector is a photomultiplier.

23. The microscope according to claim 11, wherein the coherent light source is a laser device.

24. The microscope according to claim 12, wherein the incoherent light source is a light-emitting diode.

25. The microscope according to claim 12, wherein the incoherent light source is a mercury vapour lamp.

26. The microscope according to claim 12, wherein the incoherent light source is a halogen lamp.

* * * * *